United States Patent
Suga (10) Patent No.: US 11,133,341 B2
(45) Date of Patent: Sep. 28, 2021

(54) IMAGE PICKUP APPARATUS AND MANUFACTURING METHOD OF IMAGE PICKUP APPARATUS

(71) Applicant: OLYMPUS CORPORATION, Tokyo (JP)

(72) Inventor: Kensuke Suga, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 139 days.

(21) Appl. No.: 16/687,994

(22) Filed: Nov. 19, 2019

(65) Prior Publication Data

US 2020/0083267 A1 Mar. 12, 2020

Related U.S. Application Data

(63) Continuation of application No. PCT/JP2017/019146, filed on May 23, 2017.

(51) Int. Cl.
*H01L 27/146* (2006.01)
*A61B 1/00* (2006.01)
*A61B 1/05* (2006.01)

(52) U.S. Cl.
CPC .... *H01L 27/14618* (2013.01); *H01L 27/1469* (2013.01); *H01L 27/14634* (2013.01); *H01L 27/14636* (2013.01); *A61B 1/0011* (2013.01); *A61B 1/051* (2013.01)

(58) Field of Classification Search
CPC ......... H01L 27/14618; H01L 27/14634; H01L 27/14636; H01L 27/1469; A61B 1/0011; A61B 1/051; A61B 1/04
See application file for complete search history.

(56) References Cited

U.S. PATENT DOCUMENTS 4,745,470 A 5/1988 Yabe et al.

FOREIGN PATENT DOCUMENTS

| JP | S63-065840 A | 3/1988 |
| JP | 2004-247611 A | 9/2004 |
| JP | 2007-311416 A | 11/2007 |
| JP | 2010-263020 A | 11/2010 |
| JP | 2013-030593 A | 2/2013 |
| JP | 2014-075764 A | 4/2014 |
| JP | 2014-108282 A | 6/2014 |
| JP | 2015-198726 A | 11/2015 |

OTHER PUBLICATIONS

International Search Report dated Aug. 22, 2017 issued in PCT/JP2017/019146.

*Primary Examiner* — David A Zarneke
(74) *Attorney, Agent, or Firm* — Scully, Scott, Murphy & Presser, P.C.

(57) ABSTRACT

An image pickup apparatus includes an imager, cover glass and a circuit element, the image pickup apparatus includes a first space filled with a first resin and a second space filled with a second resin, a thermal expansion coefficient of the second resin being smaller than a thermal expansion coefficient of the first resin, and when the image pickup apparatus is virtually divided into a plurality of unit columns, a ratio of the second space is larger in the unit columns in which a ratio of a space filled with resins is large than in the unit columns in which the ratio of the space filled with the resins is small.

10 Claims, 8 Drawing Sheets

FIG. 10

IMAGE PICKUP APPARATUS AND MANUFACTURING METHOD OF IMAGE PICKUP APPARATUS

CROSS REFERENCE TO RELATED APPLICATION

This application is a continuation application of PCT/JP2017/019146 filed on May 23, 2017, the entire contents of which are incorporated herein by this reference.

BACKGROUND OF INVENTION

1. Field of the Invention

The present invention relates to an image pickup apparatus in which a space between an imager and a circuit element is sealed with a resin, and a manufacturing method of the image pickup apparatus in which the space between the imager and the circuit element is sealed with the resin.

2. Description of the Related Art

At a distal end portion of an insertion portion of an endoscope, a small-sized image pickup apparatus including an imager is disposed. In recent years, an image pickup apparatus in which a circuit element that primarily processes an image pickup signal outputted by an imager is bonded to a back surface of the imager has been contemplated.

In addition, Japanese Patent Application Laid-Open Publication No. 2014-75764 describes an image pickup apparatus in which an image pickup portion on an image pickup surface and an external electrode on a back surface are connected by making a side face of an imager into an inclined surface and going through a wiring line disposed on the inclined surface.

Japanese Patent Application Laid-Open Publication No. 2013-30593 discloses a laminated element in which a plurality of semiconductor elements are laminated and respective through wiring lines are bonded in order to house the plurality of semiconductor elements in a small space and to reduce parasitic capacitance by wiring lines.

SUMMARY OF THE INVENTION

An image pickup apparatus of an embodiment of the present invention includes: an imager; cover glass laminated on one surface of the imager; and at least one circuit element laminated on another surface of the imager, wherein the image pickup apparatus includes a first space filled with a first resin and a second space in contact with the first space and filled with a second resin, a thermal expansion coefficient of the second resin being smaller than a thermal expansion coefficient of the first resin, and when the image pickup apparatus is virtually divided into a plurality of unit columns each including wall surfaces in parallel to a lamination axis, a ratio of the second space is larger in the unit columns in which a ratio of the first space and the second space is large than in the unit columns in which the ratio of the first space and the second space is small.

An image pickup apparatus of another embodiment includes: an imager; cover glass laminated on one surface of the imager; and at least one circuit element laminated on another surface of the imager, wherein the image pickup apparatus includes a third space filled with a first resin and a second resin in a first ratio, a thermal expansion coefficient of the second resin being smaller than a thermal expansion coefficient of the first resin, and a fourth space filled with the first resin and the second resin in a second ratio different from the first ratio.

A manufacturing method of an image pickup apparatus of another embodiment includes: laminating an imager and cover glass, eliminating a part of the imager, filling a space where the imager is eliminated with a second resin, laminating at least one circuit element on an opposite side of the cover glass of the imager, filling a space between the imager and the circuit element with a first resin, wherein a thermal expansion coefficient of the second resin is smaller than a thermal expansion coefficient of the first resin, and when the image pickup apparatus is virtually divided into a plurality of unit columns each including wall surfaces in parallel to a lamination axis, a ratio of the space filled with the second resin is larger in the unit columns in which the ratio of the space filled with the first resin and the second resin is large than in the unit columns in which the ratio of the space filled with the first resin and the second resin is small.

DETAILED DESCRIPTION OF THE PREFERRED EMBODIMENTS

First Embodiment

Hereinafter, an image pickup apparatus 1 of the first embodiment will be described with reference to the drawings. The drawings are schematic, and a relation between a thickness and a width of respective members, a ratio of the thicknesses of the respective members, the number of electrodes, an array pitch or the like are different from actual ones. Even among the drawings, a part where the relation of mutual dimensions or the ratio is different is included. For some components, a silicon oxide layer on a surface of an imager, for example, an illustration is omitted.

Figure 1:
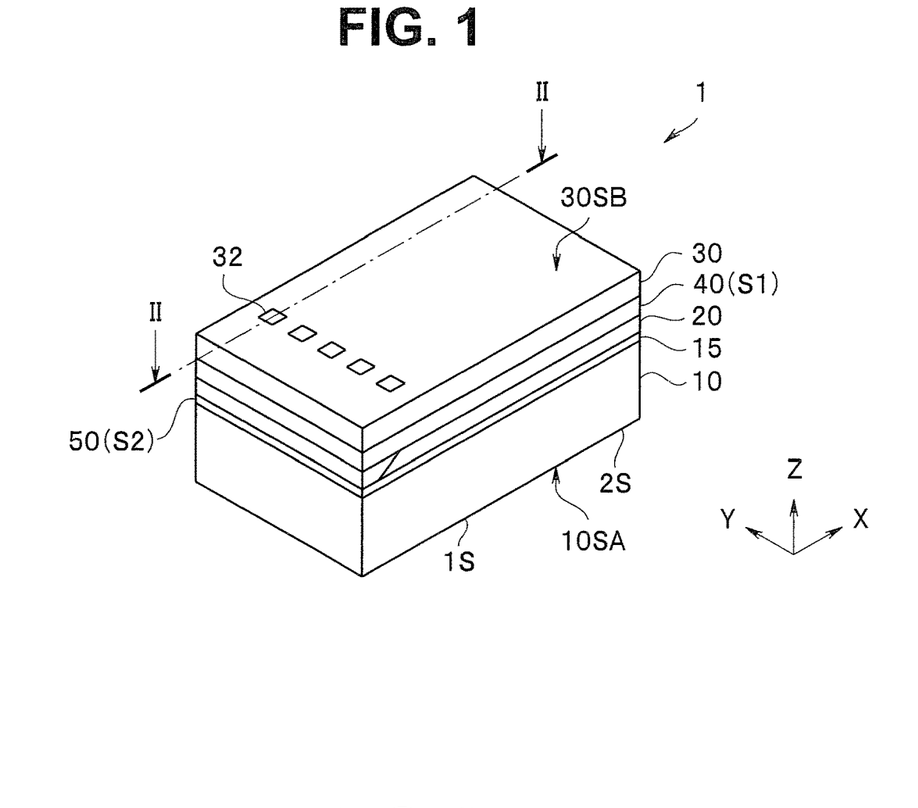
FIG. 1 is a perspective view of an image pickup apparatus of a first embodiment.
Figure 2:
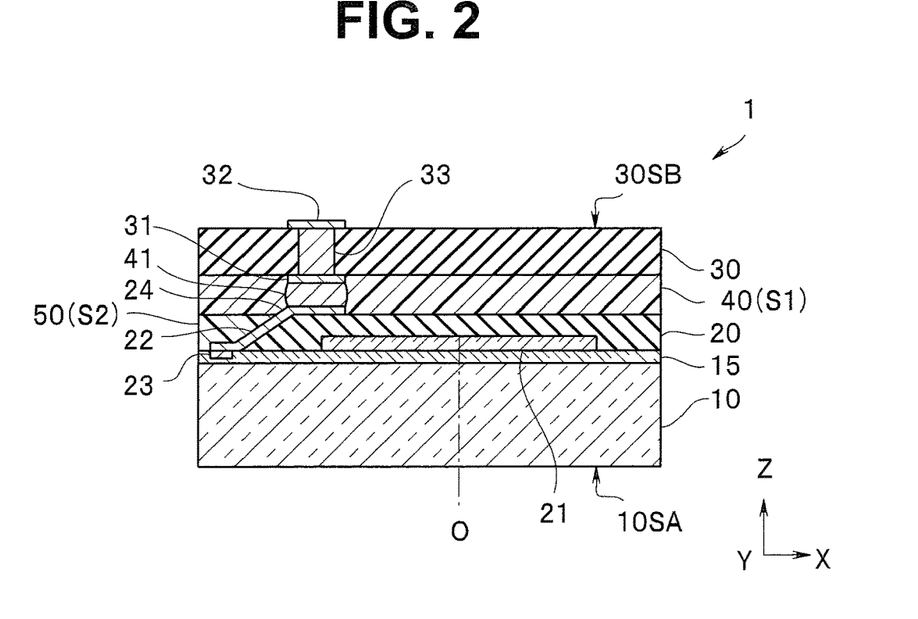
FIG. 2 is a sectional view along a II-II line in FIG. 1 of the image pickup apparatus of the first embodiment.
Figure 3:
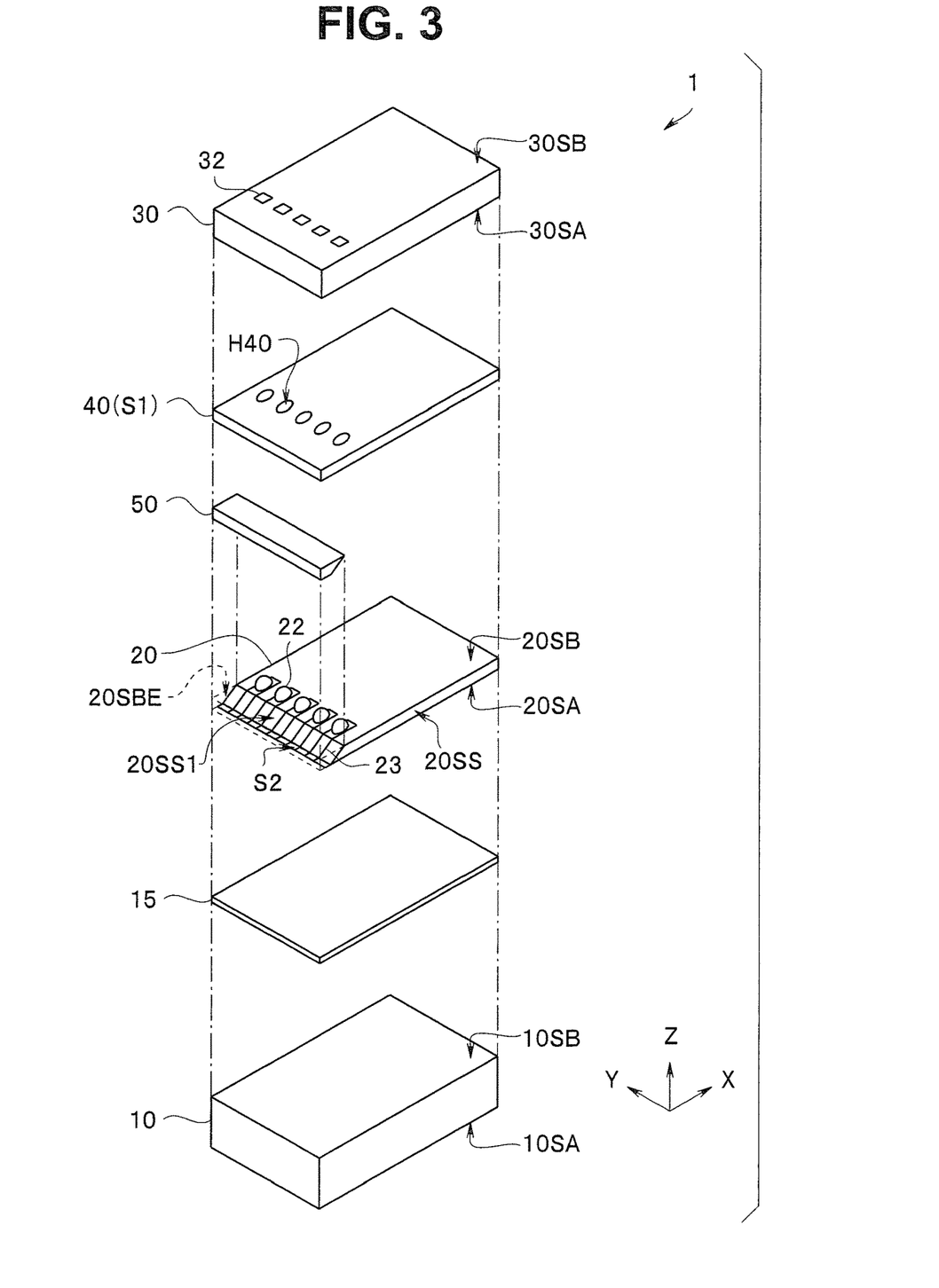
FIG. 3 is an exploded view of the image pickup apparatus of the first embodiment.

The image pickup apparatus 1 illustrated in FIG. 1, FIG. 2 and FIG. 3 is a rectangular parallelepiped including cover glass (glass chip) 10, an imager (image pickup chip) 20, and a circuit element 30. The cover glass 10 is a plate including a light receiving surface 10SA and an opposite surface 10SB on an opposite side of the light receiving surface 10SA. The imager 20, a base of which is silicon, is a plate including an image pickup surface 20SA which is one surface where an image pickup portion 21 is formed, and a back surface 20SB which is the other surface on the opposite side of the image pickup surface 20SA.

The opposite surface 10SB of the cover glass 10 is joined to the image pickup surface 20SA of the imager 20 by an adhesive layer 15 formed of a transparent resin. In other words, the cover glass 10 is laminated on the image pickup surface 20SA of the imager 20.

In the imager 20 of the image pickup apparatus 1, of four side faces 20SS, only a first side face is an inclined surface 20SS1 inclined at an obtuse angle to the back surface 20SB. On the image pickup surface 20SA, an image pickup surface electrode 23 electrically connected with the image pickup portion 21 is disposed. The image pickup surface electrode 23 is electrically connected with an external electrode 24 on the back surface 20SB by going through a wiring line 22 disposed on the inclined surface 20SS1.

The circuit element 30 is laminated on the back surface 20SB of the imager. The circuit element 30, the base of which is silicon, is a planar circuit chip including a first main surface 30SA and a second main surface 30SB opposing the first main surface 30SA. On the circuit element 30, though not illustrated, a semiconductor circuit configured to primarily process an image pickup signal outputted by the imager 20 is formed, for example. A first electrode 31 on the first main surface 30SA of the circuit element 30 is electrically connected with a second electrode 32 on the second main surface 30SB by going through a through wiring line 33. The through wiring line 33 may be electrically connected with the semiconductor circuit, or a through wiring line not illustrated may configure an internal wiring line of the semiconductor circuit.

The through wiring line 33 for which the inside of a through hole is filled with a conductor is, for example, a copper plating film disposed by a plating method. The first electrode 31 is bonded with the external electrode 24 of the imager 20 by a bump 41 which is an element bonding portion.

The image pickup apparatus 1 includes, in the inside, a first space S1 filled with a first resin 40 between the opposite surface 10SB of the cover glass 10 and the first main surface 30SA of the circuit element 30, and a second space S2 filled with a second resin 50 between the opposite surface 10SB of the cover glass 10 and the first main surface 30SA of the circuit element 30.

In other words, the space between the opposite surface 10SB of the cover glass 10 and an extension surface 20SBE of the back surface 20SB of the imager 20 including the space formed by the presence of the inclined surface 20SS1 in the imager 20 is the second space S2 filled with the second resin 50. The space between the back surface extension surface 20SBE and the first main surface 30SA is the first space S1 filled with the first resin 40.

For the second resin 50, a thermal expansion coefficient α is smaller than a thermal expansion coefficient of the first resin 40. For example, base materials of the first resin 40 and the second resin 50 are both an epoxy resin, a thermal expansion coefficient α1 of which is 50 ppm/° C., but the second resin 50 includes a filler formed of a glass fiber, the thermal expansion coefficient α of which is 3 ppm/° C. Therefore, a thermal expansion coefficient α2 of the second resin 50 is 10 ppm/° C. which is equal to or lower than 50% of the thermal expansion coefficient α1.

A thermal expansion coefficient α10 of the cover glass 10 is 2 ppm. A thermal expansion coefficient αS1 of the imager 20 and the circuit element 30 is 3.9 ppm.

As described above, in the image pickup apparatus 1, the space (S1+S2) between the opposite surface 10SB of the cover glass 10 and the second main surface 30SB of the circuit element 30 is filled with resins (the first resin 40 and the second resin 50).

A manufacturing method of the image pickup apparatus 1 will be simply described using FIG. 4A to FIG. 4G. Note that FIG. 4A or the like is a partial sectional view of a wafer. In other words, the image pickup apparatus 1 of a W-CSP type (wafer level chip size package type) is manufactured by cutting a bonded wafer 1W for which a glass wafer 10W, an image pickup wafer 20W including the plurality of imagers 20 and an element wafer 30W including the plurality of circuit elements 30 are bonded (see FIG. 4G). The image pickup apparatus 1 may not be manufactured by cutting the bonded wafer 1W but the image pickup apparatus 1 may be manufactured by separately cutting the image pickup wafer 20W to which the glass wafer 10W is bonded and the element wafer 30W and then bonding the wafers.

Figure 4A:
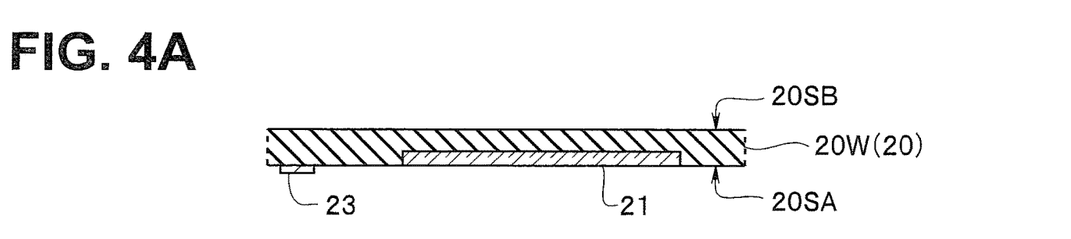
FIG. 4A is a sectional view for explaining a manufacturing method of the image pickup apparatus of the first embodiment.

As illustrated in FIG. 4A, the plurality of image pickup portions 21 formed of a CMOS (complementary metal oxide semiconductor) image sensor or a CCD (charge coupled device) or the like are formed on a silicon wafer. The plurality of image pickup surface electrodes 23 configured to supply an electric signal to the image pickup portions 21 and transmit the image pickup signal from the image pickup portions 21 are disposed on the image pickup surface 20SA around the respective image pickup portions 21, and the image pickup wafer 20W including the plurality of imagers 20 is manufactured.

Figure 4B:
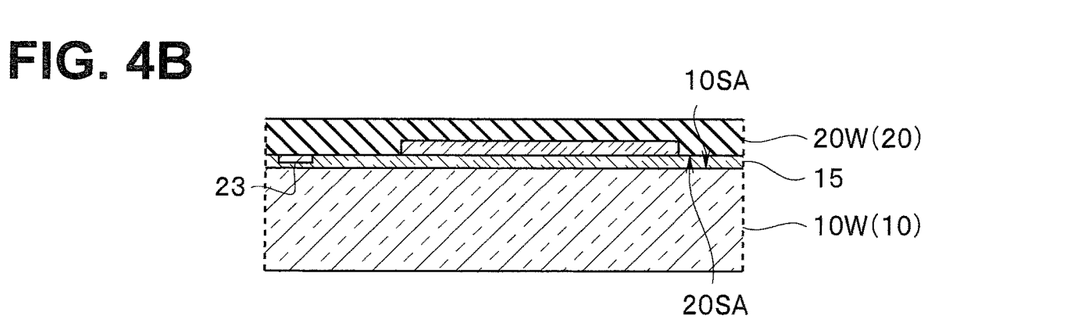
FIG. 4B is a sectional view for explaining the manufacturing method of the image pickup apparatus of the first embodiment.

As illustrated in FIG. 4B, the glass wafer 10W is joined to the image pickup surface 20SA of the image pickup wafer 20W by the adhesive layer 15 formed of a transparent ultraviolet curing type resin. A microlens array may be disposed on the image pickup portions 21 and only a periphery of the image pickup portions 21 may be joined with the glass wafer 10W by a light-shielding adhesive material.

Figure 4C:
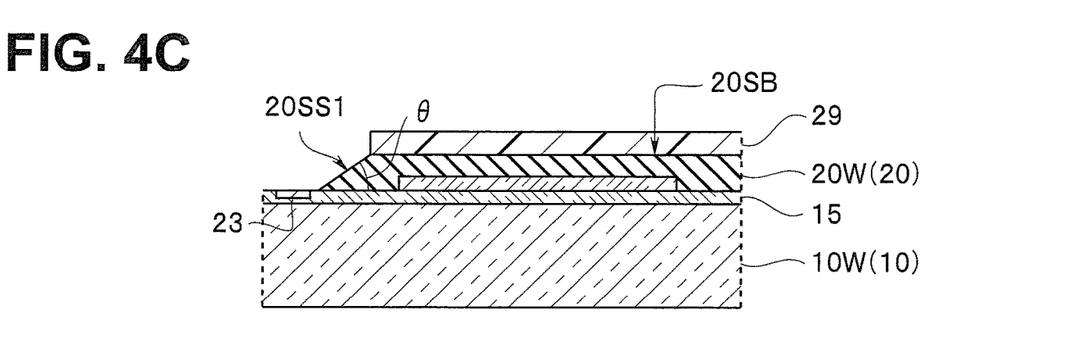
FIG. 4C is a sectional view for explaining the manufacturing method of the image pickup apparatus of the first embodiment.

As illustrated in FIG. 4C, an etching mask 29 is disposed on the back surface 20SB of the image pickup wafer 20W. Then, as illustrated in FIG. 4C, by eliminating a part of the imager into a state of exposing a back surface of the image pickup surface electrodes 23 to a back surface side, a through trench, a wall surface of which is the inclined surface 20SS1, is formed. By etching, that is, by formation of the inclined surface 20SS1, the second space S2 is generated. In other words, the space where a part of the imager 20 is eliminated by the etching is the second space S2.

For formation of the through trench including the inclined surface 20SS1, it is preferable to use anisotropic etching. As the anisotropic etching, a wet etching method using a tetramethylammonium hydroxide (TMAH) solution, a potassium hydroxide (KOH) solution or the like is desirable, but a dry etching method such as reactive ion etching (RIE) or chemical dry etching (CDE) may be used.

For example, when a silicon substrate for which the image pickup surface 20SA is a (100) plane is used as the imager 20, since an etching speed of a (111) plane is slow compared to the (100) plane in the anisotropic etching, the wall surface of the through trench becomes the (111) plane, and the wall surface becomes the inclined surface 20SS1 for which an angle θ formed with the (100) plane which is a surface (back surface 20SB) where the circuit element 30 is laminated is an obtuse angle of 125.3 degrees.

Figure 4D:
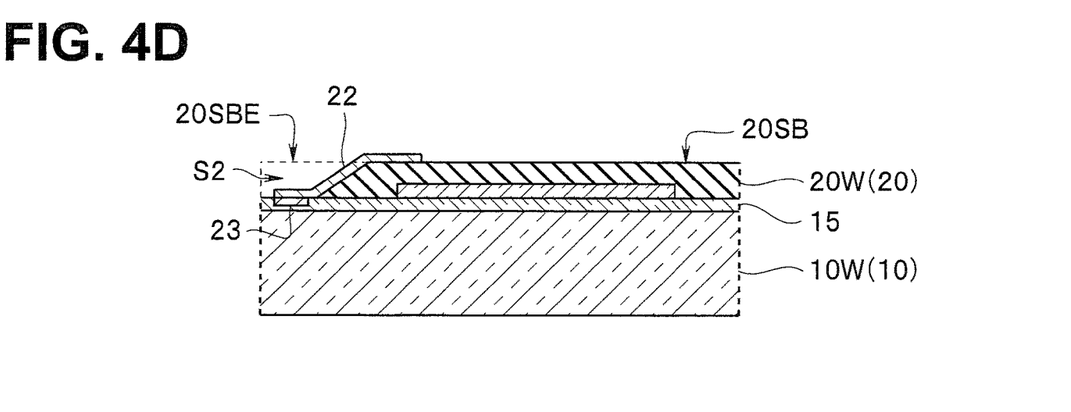
FIG. 4D is a sectional view for explaining the manufacturing method of the image pickup apparatus of the first embodiment.

Next, as illustrated in FIG. 4D, the wiring line 22 is disposed from the back surface of the image pickup surface electrodes 23 through the inclined surface 20SS1 to the back surface 20SB. Since the inclined surface 20SS1 is inclined at an obtuse angle of preferably 115 degrees or greater to the back surface 20SB, the wiring line 22 is not disconnected at a boundary between the inclined surface 20SS1 and the back surface 20SB.

For the imager 20, the plurality of wiring lines 22 connecting the image pickup surface 20SA and the back surface 20SB are disposed on the inclined surface 20SS1 forming the obtuse angle to the back surface 20SB. Formation of a wiring layer and patterning of the wiring layer by photolithography for disposing the wiring lines 22 are performed to the inclined surface. Therefore, compared to an imager for which the plurality of wiring lines 22 are disposed to a wall surface vertical to the back surface 20SB, the imager 20 is easy to manufacture.

In the imager 20, a part of the wiring line 22 on the back surface 20SB is the external electrode 24. The external electrode 24 may be configured by disposing a (gold/nickel) film further on a part of the wiring line 22 on the back surface 20SB. Then, the bump 41 which is the element bonding portion is disposed to the external electrode 24. The bump 41 is, for example, a solder bump or a gold bump formed by a frame plating method or a paste printing method.

Figure 4E:
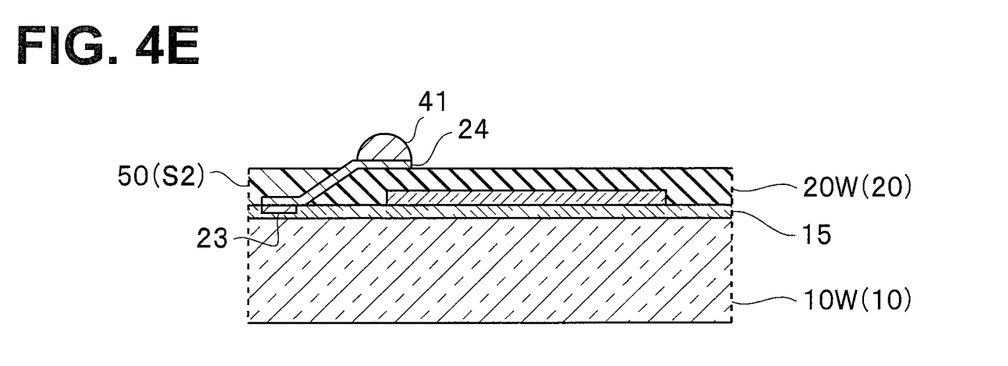
FIG. 4E is a sectional view for explaining the manufacturing method of the image pickup apparatus of the first embodiment.

As illustrated in FIG. 4E, the second space S2 is filled with the second resin 50 to be cured. The second resin 50 is an epoxy resin including the filler formed of the glass fiber.

Figure 4F:
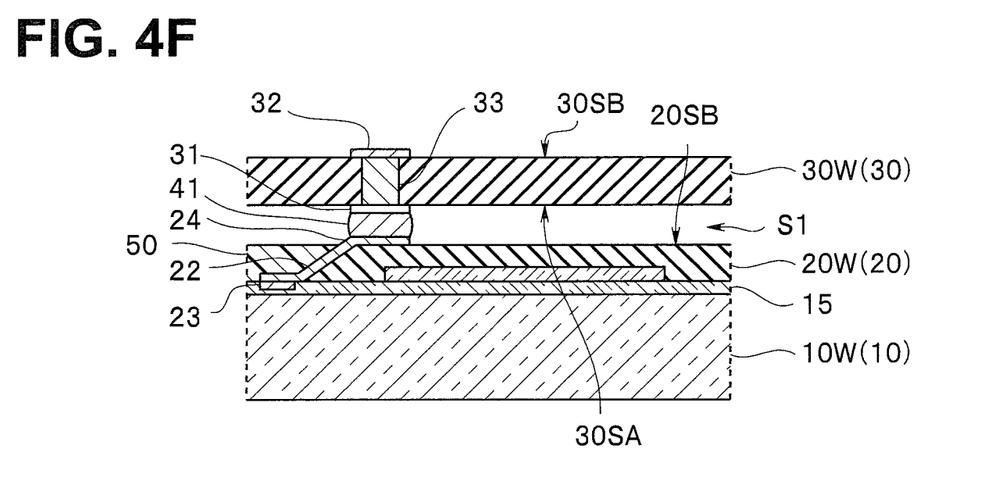
FIG. 4F is a sectional view for explaining the manufacturing method of the image pickup apparatus of the first embodiment.

As illustrated in FIG. 4F, the element wafer 30W including the plurality of circuit elements 30 includes the through wiring line 33 passing through the first main surface 30SA and the second main surface 30SB. For the through wiring line 33, after a through hole is formed, for example, a conductive film is disposed to the wall surface, and an electroplating film is disposed in the state of filling the inside of the through hole.

To the image pickup wafer 20W, the element wafer 30W is bonded by the bump 41 which is the element bonding portion. For example, on the element wafer 30W formed of silicon, though not illustrated, a semiconductor circuit such as an AD conversion circuit, a memory, a transmission output circuit, a filter circuit, a thin film capacitor or a thin film inductor is formed.

The space between the back surface 20SB of the image pickup wafer 20W and the first main surface 30SA of the element wafer 30W is the first space S1.

Figure 4G:
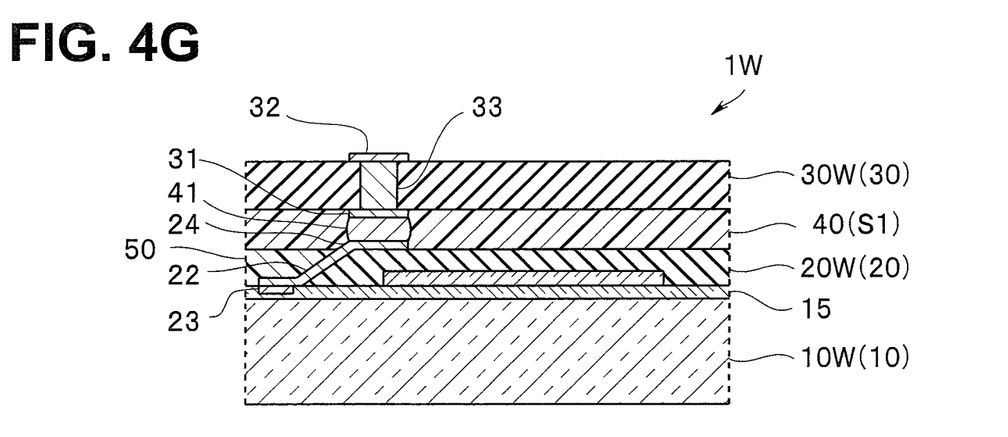
FIG. 4G is a sectional view for explaining the manufacturing method of the image pickup apparatus of the first embodiment.

As illustrated in FIG. 4G, in the first space S1, the first resin 40 formed of an epoxy resin is injected and cured as a side-fill resin. The first resin 40 is a sealing resin that seals a bonding portion, and is also a joining resin that joins the image pickup wafer 20W and the element wafer 30W.

Note that the first resin 40 may be an NCF (non-conductive film) disposed between the image pickup wafer 20W and the element wafer 30W upon bonding.

As the first resin 40 and the second resin 50, a polyimide resin, a phenol resin, a silicone resin, or an acrylic resin or the like may be used. In addition, the first resin 40 and the second resin 50 may include the filler, and since a filler content rate of the second resin 50 is higher than a filler content rate of the first resin 40, the thermal expansion coefficient may be small. Note that as long as the filler is an insulator of the thermal expansion coefficient smaller than the thermal expansion coefficient of the resin, the filler may be ceramic such as alumina, is not limited to be fibrous, but may be spherical or amorphous. The filler may be spherical glass or the like having a negative thermal expansion coefficient, that is, the spherical glass or the like, the volume of which is reduced by heating.

Further, two kinds of resins of different thermal expansion coefficients may be used as the first resin 40 or the second resin 50. For example, when the first resin 40 is a polyurethane resin ($\alpha$=100 ppm/° C.), as the second resin 50, the epoxy resin, a polycarbonate resin ($\alpha$=55 ppm/° C.) or a urea resin ($\alpha$=25 ppm/° C.) is used. By adding the filler further to the resin of the smaller thermal expansion coefficient of the two kinds of the resins of the different thermal expansion coefficients or adding a larger amount of the filler than the filler added to the first resin 40, the resin may be used as the second resin 50.

Note that by adding the filler, thermal conductivity of which is higher than the thermal conductivity of the resin, the thermal conductivity of the second resin 50 becomes higher than the thermal conductivity of the first resin 40. Therefore, heat generated by the imager 20 can be efficiently transmitted by passing through a frame member formed of a metal, for example.

Then, by cutting processing of the bonded wafer 1W illustrated in FIG. 4G, the image pickup apparatus 1 illustrated in FIG. 2 is manufactured. In the image pickup apparatus 1 of the W-CSP type, four side faces are identical cut sections, and external sizes of a plurality of laminated members (the cover glass 10, the imager 20 and the circuit element 30) are the same.

As described above, in the manufacturing method of the image pickup apparatus 1, the imager and the cover glass are laminated, a part of the imager is eliminated, the space where the imager is eliminated is filled with the second resin, at least one circuit element is laminated on the opposite side of the cover glass of the imager, and the space between the imager and the circuit element is filled with the first resin.

In the image pickup apparatus 1, the volume (a resin thickness) of the space filled with the resin is deflected in an in-plane direction (XY direction) orthogonal to an optical axis O. In other words, in the image pickup apparatus 1, the inclined surface 20SS1 is formed only on a first side face 20SS1 of the four side faces of the imager 20. Therefore, the second resin 50 is deflected and disposed in the in-plane direction vertical to the optical axis (Z axis) 0 of the imager 20. In other words, there is an in-plane distribution of the space (volume) occupied by the resin.

The part where the ratio (a volume ratio in a predetermined space) occupied by the resin is large expands with heat greatly compared to the part where the ratio is small. Therefore, large thermal stress is generated in the in-plane direction. Then, there is a risk that detachment occurs at an interface of the resin or the like.

However, in the image pickup apparatus 1, in the part where the ratio occupied by the resin is large (the space where the volume ratio of the resin is large), the ratio of the second resin 50 of the small thermal expansion coefficient to the entire resin is large, compared to the part (space) where the ratio is small Thus, in the image pickup apparatus 1, the thermal stress in the in-plane direction is small and reliability is excellent.

Note that it is preferable that the thermal expansion coefficient α2 of the second resin 50 is equal to or lower than 50% of the thermal expansion coefficient α1 of the first resin 40 and is further preferably equal to or lower than 30%.

Figure 5:
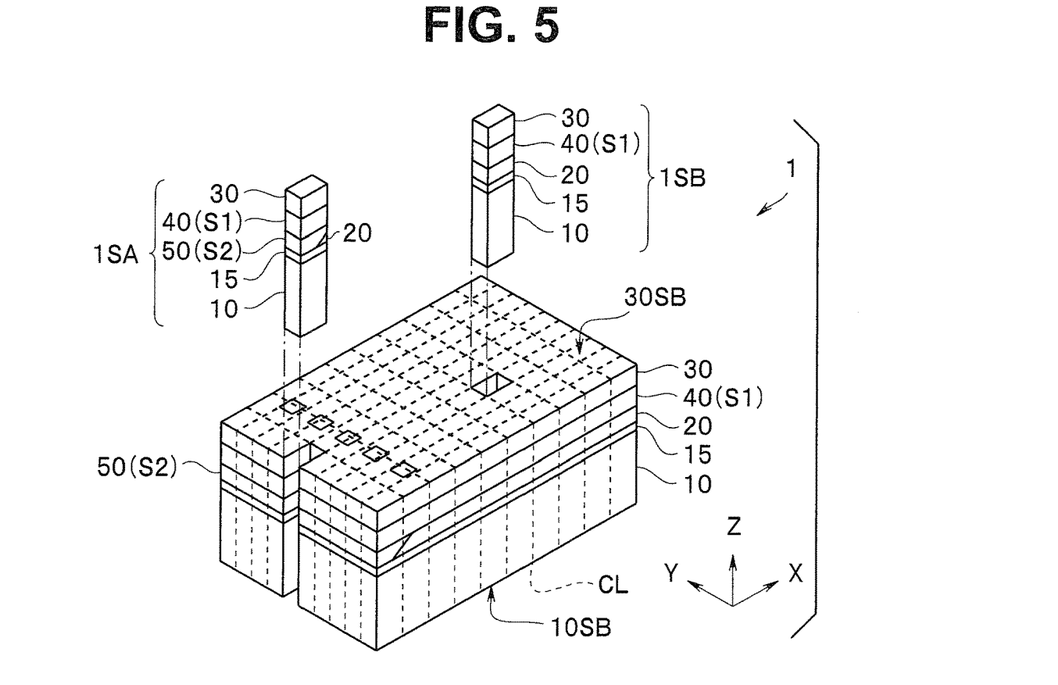
FIG. 5 is a perspective view for explaining a configuration of the image pickup apparatus of the first embodiment.

In other words, in the image pickup apparatus 1 illustrated in FIG. 5, when the image pickup apparatus 1 is virtually divided into a plurality of unit columns S each including the wall surfaces in parallel to a lamination axis, the ratio of the second space S2 filled with the second resin 50 is larger in the unit columns in which the ratio of the space (S1+S2) filled with the resin is large, a unit column 1SA, for example, than in the unit columns in which the ratio of the space (S1+S2) filled with the resin is small, a unit column 1SB, for example. Note that while the image pickup apparatus 1 is divided into 100 unit rectangular columns S in FIG. 5, the number of division may be 2, for example, as long as a difference is generated in the ratio of the space filled with the resin. In addition, it is virtual division and it goes without saying that it is not needed to actually perform the cutting processing.

In other words, the image pickup apparatus 1 includes, in the inside, a third space filled with the first resin and the second resin in a first ratio, the thermal expansion coefficient of the second resin being smaller than the thermal expansion coefficient of the first resin, and a fourth space filled with the first resin and the second resin in a second ratio different from the first ratio.

Note that the thermal expansion coefficient of the adhesive layer 15 formed of the transparent resin is also larger than the thermal expansion coefficient of the cover glass 10 and the thermal expansion coefficient of the imager 20. However, since the thickness of the adhesive layer 15 is uniform, the thermal stress in the in-plane direction due to the adhesive layer 15 is hardly generated.

The image pickup apparatus 1 is highly reliable since influence by the thermal stress is small.

The second resin 50 of the small thermal expansion coefficient is sometimes not good in terms of adhesive properties, sealing properties (water vapor isolation) and cost, compared to the first resin 40. However, since the second resin 50 is used only partially in the image pickup apparatus 1, it is not a big problem.

Second Embodiment

Since an image pickup apparatus 2 of the second embodiment is similar to the image pickup apparatus 1 and has the same effect, the same signs are attached to components of the same functions and description is omitted.

Figure 6:
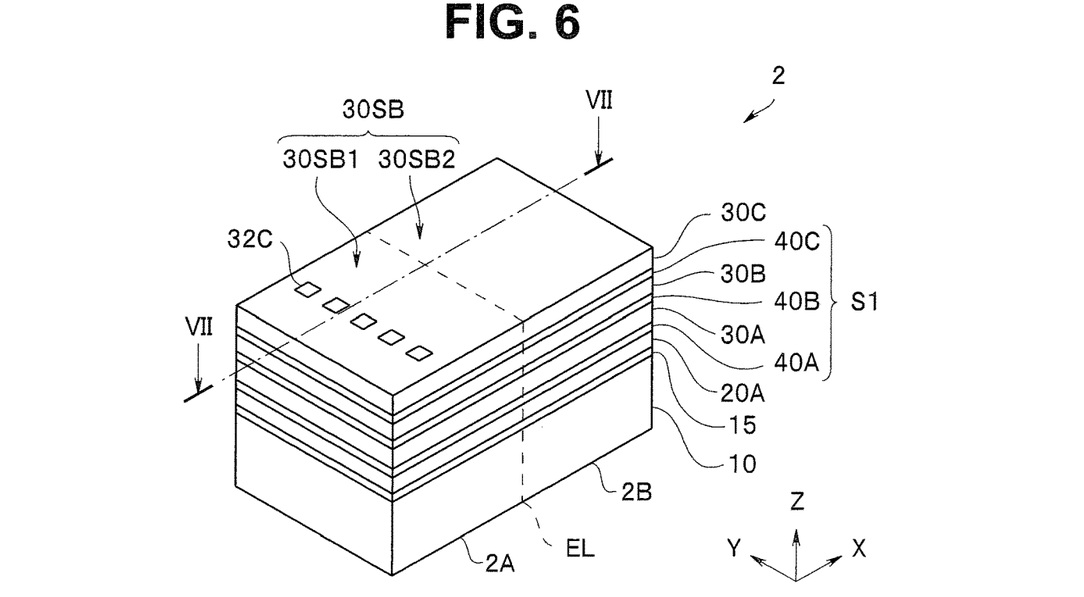
FIG. 6 is a perspective view of an image pickup apparatus of a second embodiment.
Figure 7:
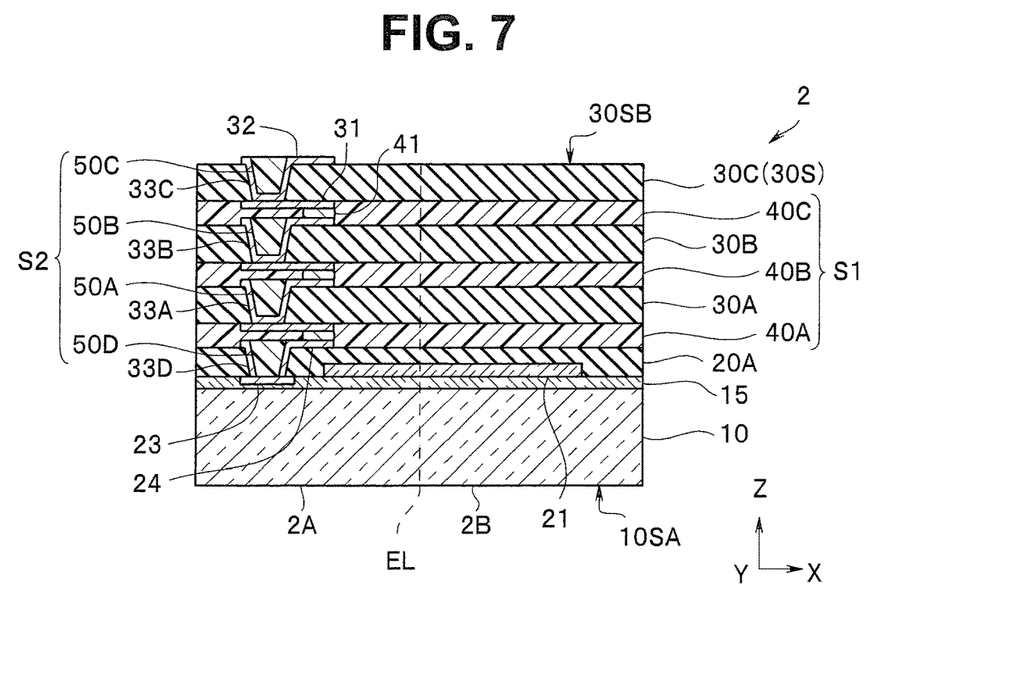
FIG. 7 is a sectional view along a VII-VII line in FIG. 6 of the image pickup apparatus of the second embodiment.

In the image pickup apparatus 2 illustrated in FIG. 6 and FIG. 7, the image pickup surface electrode 23 of an imager 20A is connected with the external electrode 24 by going through a through wiring line 33D.

The image pickup apparatus 2 includes a rectangular parallelepiped laminated element 30S in which a plurality of planar circuit elements (circuit chips) 30A to 30C are laminated and respective through wiring lines 33A to 33C are connected by the plurality of element joining portions sealed with first resins 40A to 40C. In other words, in the laminated element 30S, the plurality of circuit elements 30A to 30C each including the through wiring lines 33A to 33C are laminated holding the first resins 40A to 40C between the respective circuit elements.

The image pickup apparatus 2 of the W-CSP type is, similarly to the image pickup apparatus 1, the rectangular parallelepiped manufactured by the cutting processing of the bonded wafer for which a glass wafer, an image pickup wafer including the plurality of imagers 20A and a plurality of element wafers each including the plurality of circuit elements 30A to 30C are bonded.

In the image pickup apparatus 2, when the first main surface 30SA (the light receiving surface 10SA) and the second main surface 30SB are bisected by virtual division into a first area 2A and a second area 2B including a wall surface (EL) in parallel to the lamination axis of the circuit elements 30A to 30C, the through wiring lines 33A to 33D are arranged only in the first area 2A which is one of the first area 2A and the second area 2B.

The through wiring lines 33A to 33D are a conductor layer in which the wall surface of the through hole is formed, and the through hole is filled with second resins 50A to 50D. In other words, the through hole is not filled with a conductor.

Figure 8:
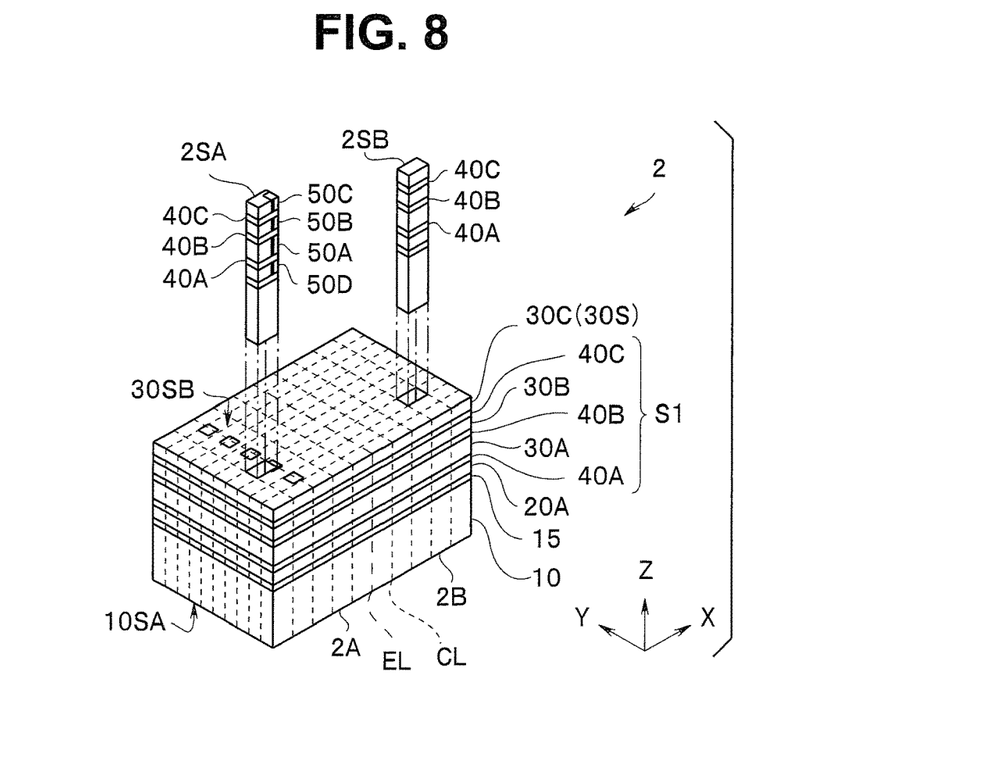
FIG. 8 is a perspective view for explaining a configuration of the image pickup apparatus of the second embodiment.

Therefore, in the image pickup apparatus 2 illustrated in FIG. 8, when the image pickup apparatus 2 is virtually divided into the plurality of unit columns S, respective long axes (wall surfaces) of which are in parallel to the optical axis (lamination axis), the ratio of the second space S2 filled with the second resin 50 is larger in the unit columns in which the ratio of the space (S1+S2) filled with the resin is large, a unit column 2SA, for example, than in the unit columns in which the ratio of the space (S1+S2) filled with the resin is small, a unit column 2SB, for example.

In the image pickup apparatus 2, the volume (the resin thickness) of the space filled with the resin is deflected in the in-plane direction (XY direction) orthogonal to the optical axis O. In other words, in the image pickup apparatus 2, the through wiring lines 33A to 33D filled with the resin are arranged only in the first area 2A. Therefore, the second resin 50 is deflected and disposed in the in-plane direction vertical to the optical axis (Z axis) O of the imager 20A. In other words, there is the in-plane distribution of the space filled with the resin.

However, in the image pickup apparatus 2, in the part (space) where the ratio occupied by the resin is large, the ratio of the second resin 50 of the small thermal expansion coefficient to the entire resin is large, compared to the part (space) where the ratio is small. Thus, in the image pickup apparatus 2, the thermal stress in the in-plane direction is small and the reliability is excellent.

Third Embodiment

Since an image pickup apparatus 3 of the third embodiment is similar to the image pickup apparatuses 1 and 2 and has the same effect, the same signs are attached to components of the same functions and description is omitted.

Figure 9:
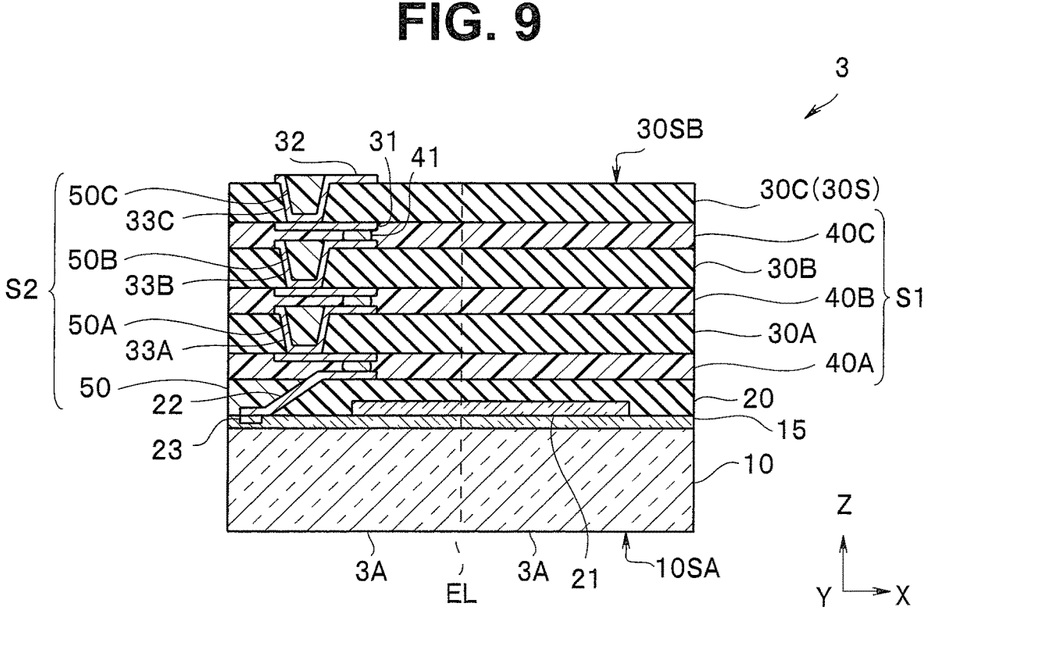
FIG. 9 is a sectional view of an image pickup apparatus of a third embodiment.

The image pickup apparatus 3 illustrated in FIG. 9 includes the imager 20 the same as the image pickup apparatus 1 and the laminated element 30S the same as the image pickup apparatus 2.

Therefore, in the image pickup apparatus 3, the thermal stress in the in-plane direction is small and the reliability is excellent.

Fourth Embodiment

Figure 10:
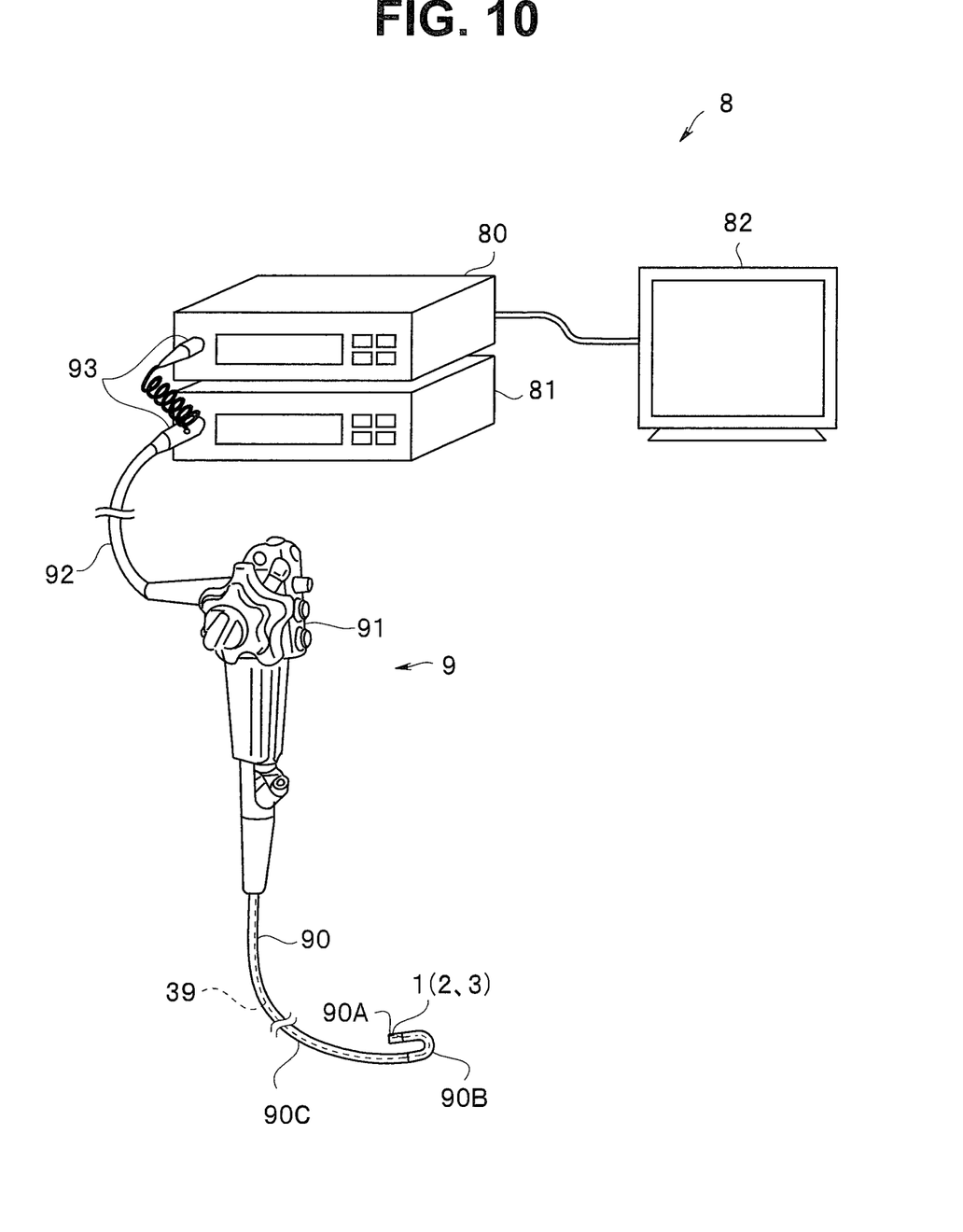
FIG. 10 is a perspective view of an endoscope of a fourth embodiment.

An endoscope system 8 including an endoscope 9 of the present embodiment illustrated in FIG. 10 includes the endoscope 9, a processor 80, a light source device 81, and a monitor 82. The endoscope 9 includes an insertion portion 90, an operation portion 91 and a universal cord 92. The insertion portion 90 is inserted into a body cavity of a subject, and the endoscope 9 photographs an in-vivo image of the subject and outputs an image signal.

The insertion portion 90 is configured by a distal end portion 90A where the image pickup apparatus 1, 2 or 3 (hereinafter, referred to as the image pickup apparatus 1 or the like) is disposed, a freely bendable bending portion 90B connected to a proximal end side of the distal end portion 90A, and a flexible portion 90C connected to the proximal end side of the bending portion 90B. The bending portion 90B is bent by an operation of the operation portion 91. Note that the endoscope 9 may be a rigid endoscope or may be a capsule type endoscope.

On the proximal end side of the insertion portion 90 of the endoscope 9, the operation portion 91 provided with various kinds of buttons that operate the endoscope 9 is disposed.

The light source device 81 includes a white LED, for example. Illumination light emitted by the light source device 81 is guided to the distal end portion 90A by going through a light guide (not illustrated) inserted through the universal cord 92 and the insertion portion 90, and illuminates the subject.

The endoscope 9 includes the insertion portion 90, the operation portion 91 and the universal cord 92, and transmits the image pickup signal outputted by the image pickup apparatus 1 or the like disposed in the distal end portion 90A of the insertion portion 90 through a signal cable 39 inserted through the insertion portion 90.

Since the image pickup apparatus 1 or the like is highly reliable, the endoscope 9 is highly reliable.

The present invention is not limited to the above-described embodiments or the like, but can be variously changed, altered or combined or the like without changing a subject matter of the present invention.

What is claimed is:

1. An image pickup apparatus comprising:
   an imager;
   cover glass laminated on one surface of the imager; and
   at least one circuit element laminated on another surface of the imager,
   wherein the image pickup apparatus includes a first space filled with a first resin and a second space in contact with the first space and filled with a second resin, a thermal expansion coefficient of the second resin being smaller than a thermal expansion coefficient of the first resin, and
   when the image pickup apparatus is virtually divided into a plurality of unit columns each including wall surfaces in parallel to a lamination axis, a ratio of the second space is larger in the unit columns in which a ratio of the first space and the second space is large than in the unit columns in which the ratio of the first space and the second space is small.

2. The image pickup apparatus according to claim 1, wherein the thermal expansion coefficient of the second resin is equal to or lower than 50% of the thermal expansion coefficient of the first resin.

3. The image pickup apparatus according to claim 2, wherein a filler content rate of the first resin is different from a filler content rate of the second resin.

4. The image pickup apparatus according to claim 1, wherein a space where a part of the imager is eliminated is filled with the second resin.

5. The image pickup apparatus according to claim 1, comprising
   a laminated element in which the plurality of circuit elements each having a through wiring line are laminated holding the first resin between the respective circuit elements,
   wherein, when bisection is performed by virtual division into a state where respective parts include a wall surface in parallel to the lamination axis, the through wiring line is arranged only in one part, and the through wiring line is filled with the second resin.

6. An image pickup apparatus comprising:
   an imager;
   cover glass laminated on one surface of the imager; and
   at least one circuit element laminated on another surface of the imager,
   wherein the image pickup apparatus includes a third space filled with a first resin and a second resin in a first ratio, a thermal expansion coefficient of the second resin being smaller than a thermal expansion coefficient of the first resin, and a fourth space filled with the first resin and the second resin in a second ratio different from the first ratio.

7. The image pickup apparatus according to claim 6, wherein the thermal expansion coefficient of the second resin is equal to or lower than 50% of the thermal expansion coefficient of the first resin.

8. The image pickup apparatus according to claim 7, wherein a filler content rate of the first resin is different from a filler content rate of the second resin.

9. The image pickup apparatus according to claim 6, wherein a space where a part of the imager is eliminated is filled with the second resin.

10. The image pickup apparatus according to claim 6, comprising
    a laminated element in which the plurality of circuit elements each having a through wiring line are laminated holding the first resin between the respective circuit elements,
    wherein, when bisection is performed by virtual division into a state where respective parts include a wall surface in parallel to the lamination axis, the through wiring line is arranged only in one part, and the through wiring line is filled with the second resin.

* * * * *